US012311101B1

(12) United States Patent
Zhang et al.

(10) Patent No.: US 12,311,101 B1
(45) Date of Patent: May 27, 2025

(54) TRIGGER ASSEMBLY FOR INHALER, AND INHALER

(71) Applicant: SUZHOU SINGMED MEDICAL DEVICE SCIENCE AND TECHNOLOGY LTD., Suzhou (CN)

(72) Inventors: Fei Zhang, Jiangsu Province (CN); Xiaoyuan Sun, Jiangsu Province (CN); Guangtao Zhao, Jiangsu Province (CN)

(73) Assignee: SUZHOU SINGMED MEDICAL DEVICE SCIENCE AND TECHNOLOGY LTD., Suzhou (CN)

( * ) Notice: Subject to any disclaimer, the term of this patent is extended or adjusted under 35 U.S.C. 154(b) by 0 days.

(21) Appl. No.: 19/025,842

(22) Filed: Jan. 16, 2025

Related U.S. Application Data

(63) Continuation of application No. PCT/CN2024/105208, filed on Jul. 12, 2024.

(30) Foreign Application Priority Data

Jul. 3, 2024 (CN) .......................... 202410885061.4
Jul. 3, 2024 (CN) .......................... 202410885172.5

(51) Int. Cl.
*A61M 15/00* (2006.01)
*A61M 11/00* (2006.01)

(52) U.S. Cl.
CPC ........ *A61M 15/0001* (2014.02); *A61M 11/00* (2013.01); *A61M 2202/0007* (2013.01);

(Continued)

(58) Field of Classification Search
CPC .................. A61M 11/00; A61M 11/08; A61M 15/00–0001; A61M 15/009; A61M 2205/27; A61M 2205/276
See application file for complete search history.

(56) References Cited

U.S. PATENT DOCUMENTS 11,109,622 B1 * 9/2021 Woodbine ............... A24F 40/46
2007/0107720 A1 * 5/2007 Boeck ................. A61M 15/009
128/200.14

(Continued)

FOREIGN PATENT DOCUMENTS

CN 113317557 A 8/2021
CN 117550227 A 2/2024

(Continued)

*Primary Examiner* — Rachel T Sippel
(74) *Attorney, Agent, or Firm* — FisherBroyles, LLP; John K. Shimmick

(57) ABSTRACT

A trigger assembly for an inhaler and an inhaler is provided. The trigger assembly includes: a first component; a second component, the first and second components being configured such that the second component is capable of moving away from the first component to a preloaded position in the case where the second component rotates relative to the first component in a first direction; and a backstop member, which is retractably arranged in the first component to block the rotation of the second component in a second direction opposite to the first direction in the case where the second component has been moved to the preloaded position; the second component is capable of moving from the preloaded position towards the first component to a triggered position.

20 Claims, 11 Drawing Sheets

(52) U.S. Cl.
CPC . *A61M 2202/04* (2013.01); *A61M 2205/0216* (2013.01); *A61M 2205/276* (2013.01)

(56) References Cited

U.S. PATENT DOCUMENTS

| | | | |
|---|---|---|---|
| 2007/0246042 A1* | 10/2007 | Purkins | A61M 15/0073 128/200.14 |
| 2012/0136306 A1* | 5/2012 | Bartha | A61M 5/31553 604/154 |
| 2016/0089526 A1* | 3/2016 | Hofland | A61M 35/003 604/311 |
| 2016/0219934 A1 | 8/2016 | Li et al. | |
| 2022/0054775 A1* | 2/2022 | Säll | A61M 15/0096 |
| 2023/0277783 A1* | 9/2023 | Herrmann | A61M 15/002 128/200.14 |

FOREIGN PATENT DOCUMENTS

| | | |
|---|---|---|
| WO | 2017097172 A1 | 6/2017 |
| WO | 2019144378 A1 | 1/2019 |
| WO | 2024109663 A1 | 5/2024 |

* cited by examiner

A-A

TRIGGER ASSEMBLY FOR INHALER, AND INHALER

CROSS REFERENCE TO RELATED APPLICATIONS

The present application is a continuation of the international application PCT/CN2024/105208, filed on Jul. 12, 2024 and entitled "TRIGGER ASSEMBLY FOR INHALER, AND INHALER", and the international application claims the right of priority of the Chinese patent applications with the application No. 202410885061.4 filed on Jul. 3, 2024 and entitled "TRIGGER ASSEMBLY FOR INHALER, AND INHALER" and the application number 202410885172.5 filed on Jul. 3, 2024 and entitled "TRIGGER ASSEMBLY FOR INHALER, AND INHALER", the entire contents of these applications being incorporated herein by reference.

TECHNICAL FIELD

The present disclosure relates to the technical field of atomization, and in particular to a trigger assembly for an inhaler, and an inhaler.

BACKGROUND

Inhalers can atomize a liquid (e.g., a medical liquid) into droplets. In the related art, a container in an inhaler contains a liquid to be atomized or sprayed, and during the movement of the container relative to a spraying assembly, the liquid in the container can be atomized, and the atomized liquid can be sprayed out of a spray nozzle of the spraying assembly. However, triggering of this inhaler is typically unstable, resulting in that liquid spraying processes are often not smooth.

SUMMARY OF THE INVENTION

The present disclosure provides a trigger assembly for an inhaler, and an inhaler, in order to achieve reliable switching of the trigger assembly between a preloaded position and a triggered position.

According to an aspect, the present disclosure provides a trigger assembly for an inhaler. The trigger assembly includes: a first component; a second component, the first component and the second component being configured such that the second component is capable of moving away from the first component to a preloaded position in the case where the second component rotates relative to the first component in a first direction; a first elastic member, which is configured to store energy when the second component moves away from the first component; and an actuator, which is configured to block the second component from leaving the preloaded position in the case where the second component has been moved to the preloaded position, and configured to, upon being triggered, release the second component such that the second component moves to a triggered position toward the first component under the action of the first elastic member.

According to another aspect, the present disclosure provides a trigger assembly for an inhaler. The trigger assembly includes: a first component; a second component, the first component and the second component being configured such that the second component is capable of moving away from the first component to a preloaded position in the case where the second component rotates relative to the first component in a first direction; and a backstop member, which is retractably arranged in the first component to block the rotation of the second component in a second direction opposite to the first direction in the case where the second component has been moved to the preloaded position; the second component is capable of moving from the preloaded position towards the first component to a triggered position.

According to still another aspect, the present disclosure provides an inhaler, including a trigger assembly configured to trigger the inhaler to spray atomized fluid. The trigger assembly includes: a first component; a second component, the first component and the second component being configured such that the second component is capable of moving away from the first component to a preloaded position in the case where the second component rotates relative to the first component in a first direction; and a backstop member, which is retractably arranged in the first component to block the rotation of the second component in a second direction opposite to the first direction in the case where the second component has been moved to the preloaded position; the second component is capable of moving from the preloaded position towards the first component to a triggered position.

BRIEF DESCRIPTION OF THE DRAWINGS

More details, features and advantages of the present disclosure are disclosed in the following description of example embodiments with reference to the accompanying drawings, in which.

DETAILED DESCRIPTION

In the present disclosure, unless otherwise stated, the terms "first", "second", etc., used to describe various elements are not intended to limit the positional, temporal or importance relationship of these elements, but rather only to distinguish one component from another. In some examples, a first element and a second element may refer to a same instance of the element, and in some cases, based on contextual descriptions, the first element and the second element may also refer to different instances.

In the scope of the present disclosure, a "inhaler" refers to an apparatus for atomizing a liquid. Typically, the inhaler is configured to atomize a fluid (e.g., a liquid drug or similar fluid) and spray the atomized fluid to the mouth or nose of a user (e.g., a patient).

The present disclosure provides a trigger assembly for an inhaler, and an inhaler. In the scope of the present disclosure, a "trigger assembly" refers to an assembly for controlling the triggering of the inhaler, for example, an assembly capable of controlling or preventing spraying operation of the inhaler. The trigger assembly can be mounted in the inhaler and can be in linkage with a push switch or rotary switch of the inhaler. Herein, a second component is blocked from leaving a preloaded position by an actuator in the case where the second component has been moved to the preloaded position, and the second component is released upon the actuator being triggered, such that the second component moves to a triggered position toward a first component, to achieve reliable switching of the trigger assembly between the preloaded position and the triggered position.

Figure 1:
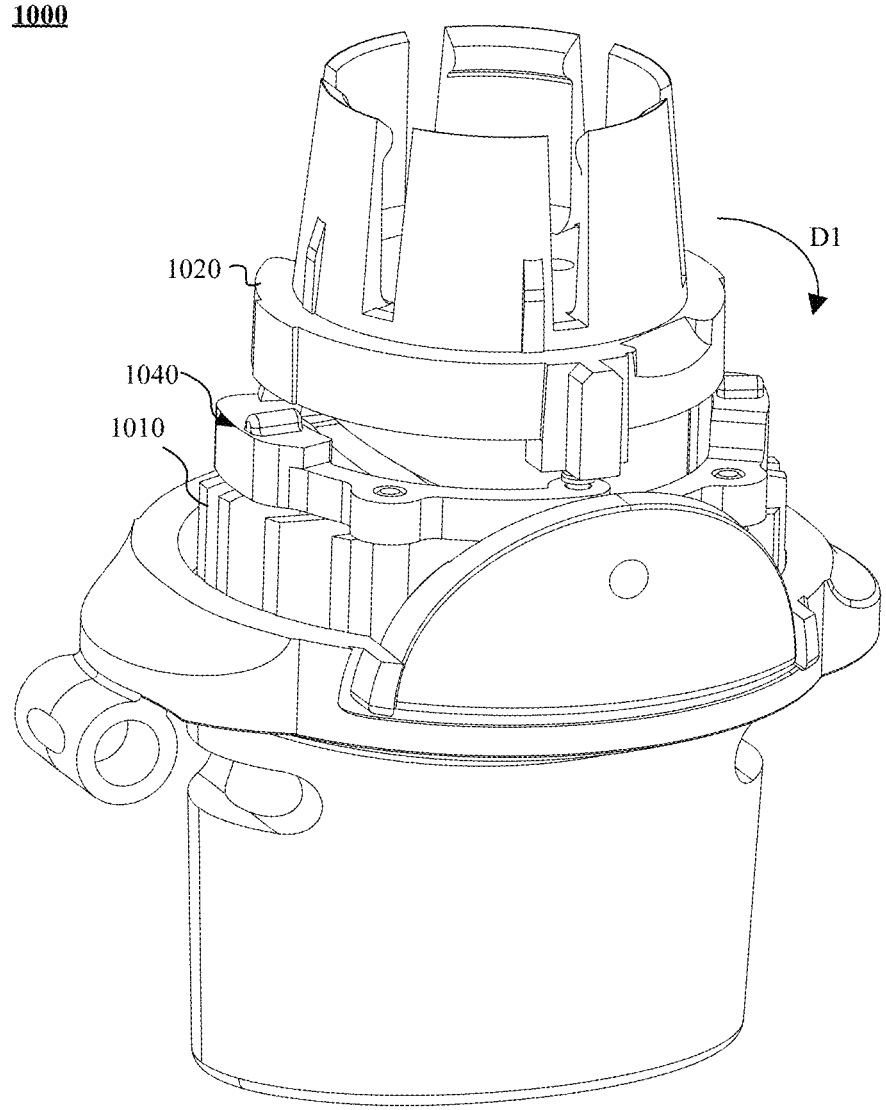
FIG. 1 is a schematic diagram illustrating a trigger assembly for an inhaler in a triggered position state according to an example embodiment.
Figure 2:
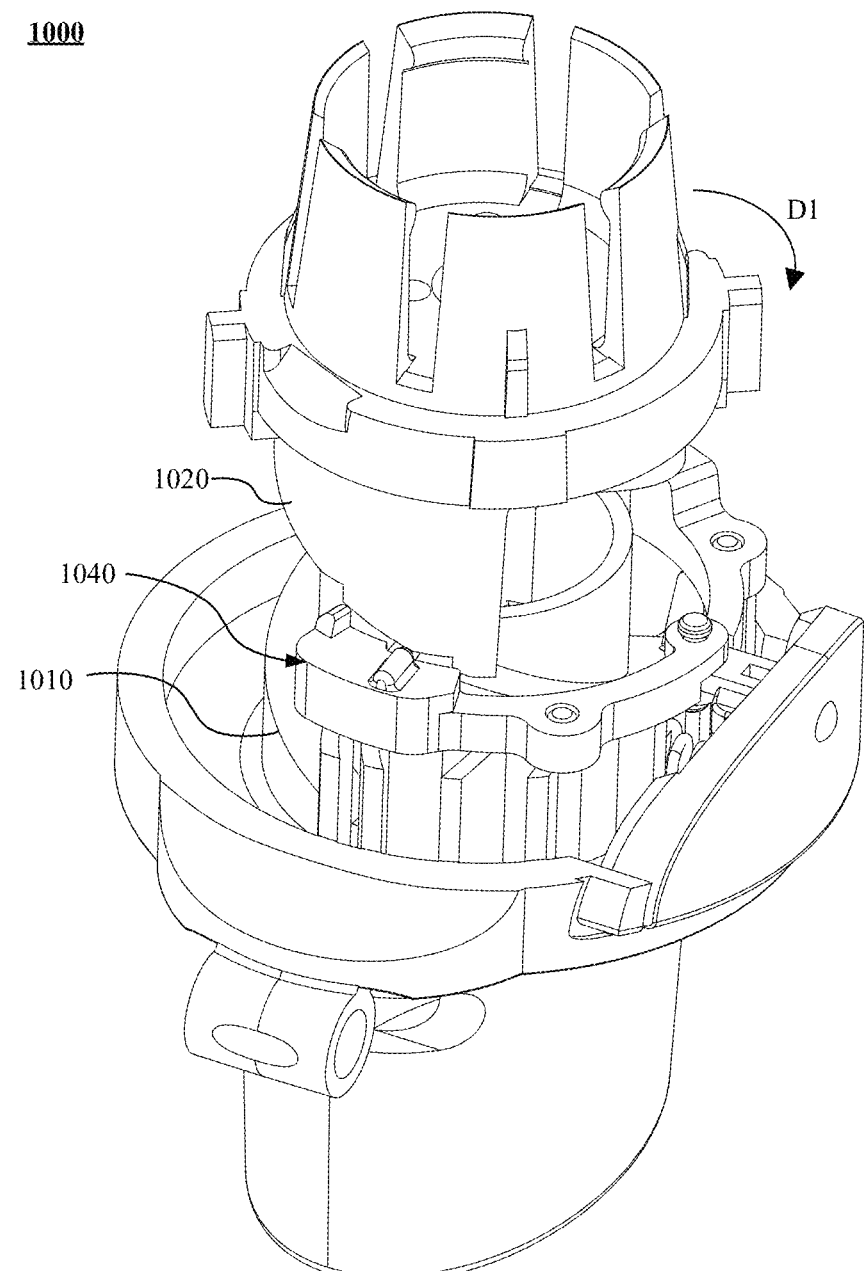
FIG. 2 is a schematic diagram illustrating a trigger assembly for an inhaler in an intermediate state according to an example embodiment.
Figure 3:
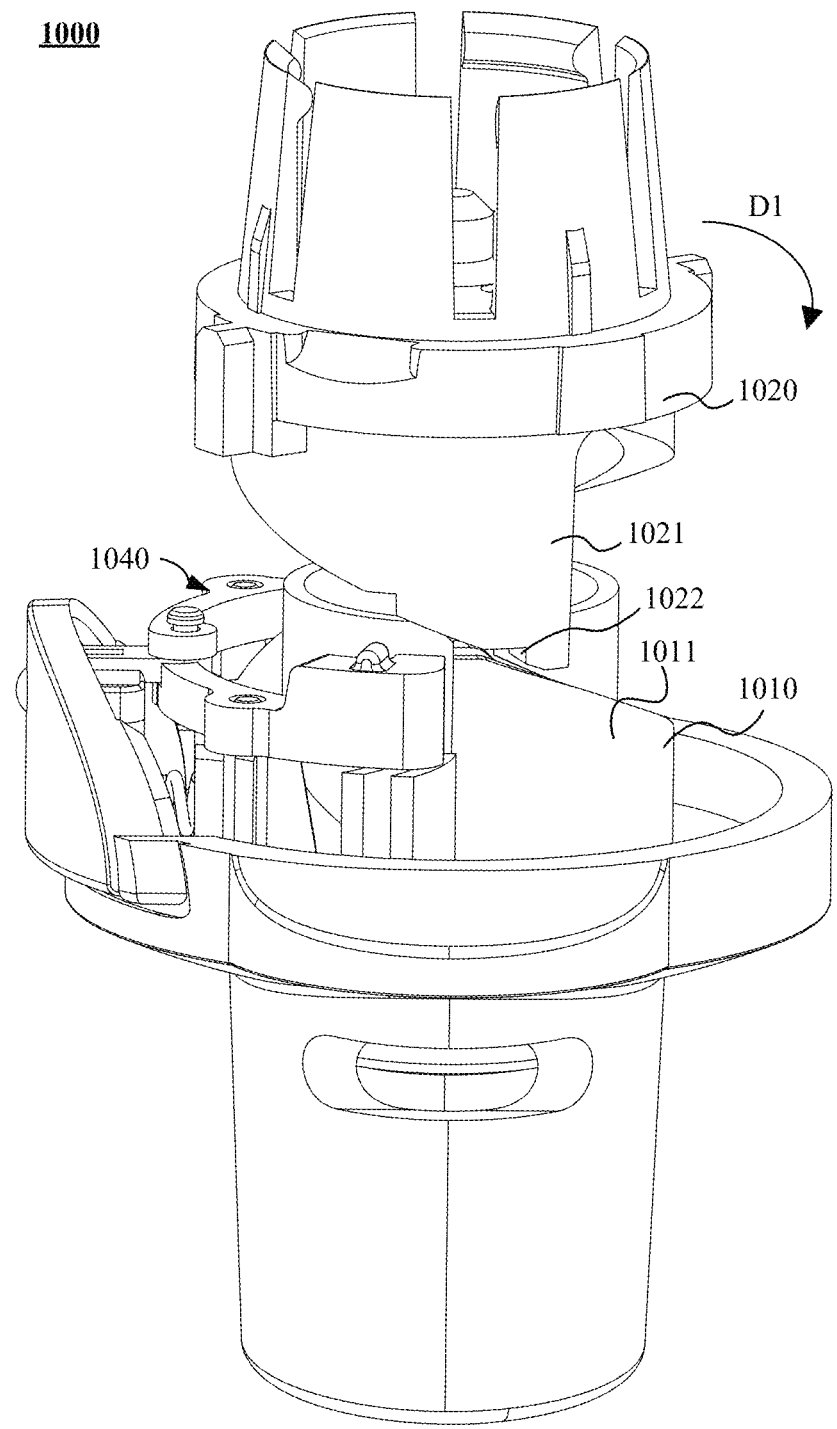
FIG. 3 is another schematic diagram illustrating a trigger assembly for an inhaler in an intermediate state according to an example embodiment.
Figure 4:
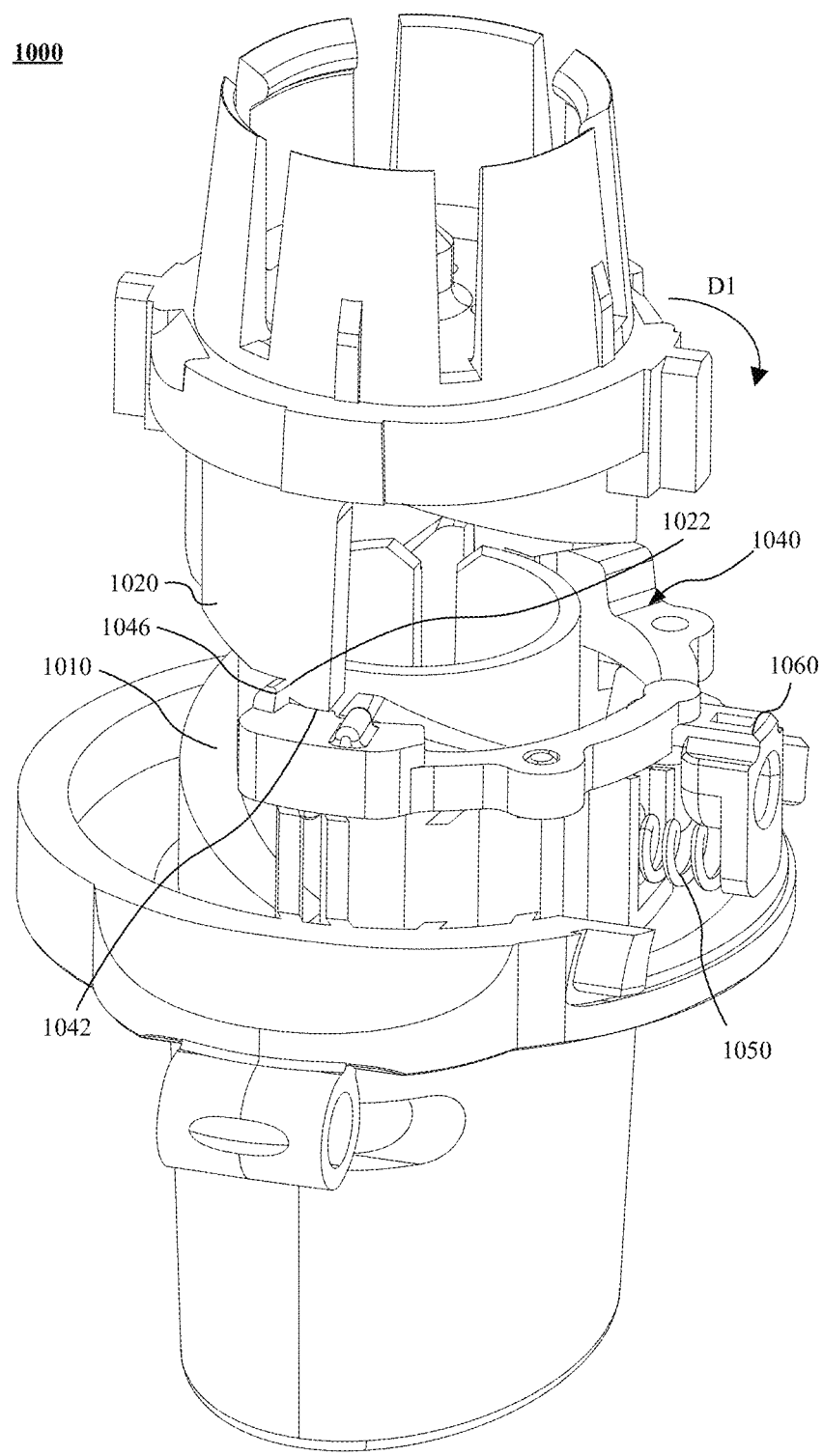
FIG. 4 is a schematic diagram illustrating a trigger assembly for an inhaler in a preloaded position state according to an example embodiment.
Figure 5:
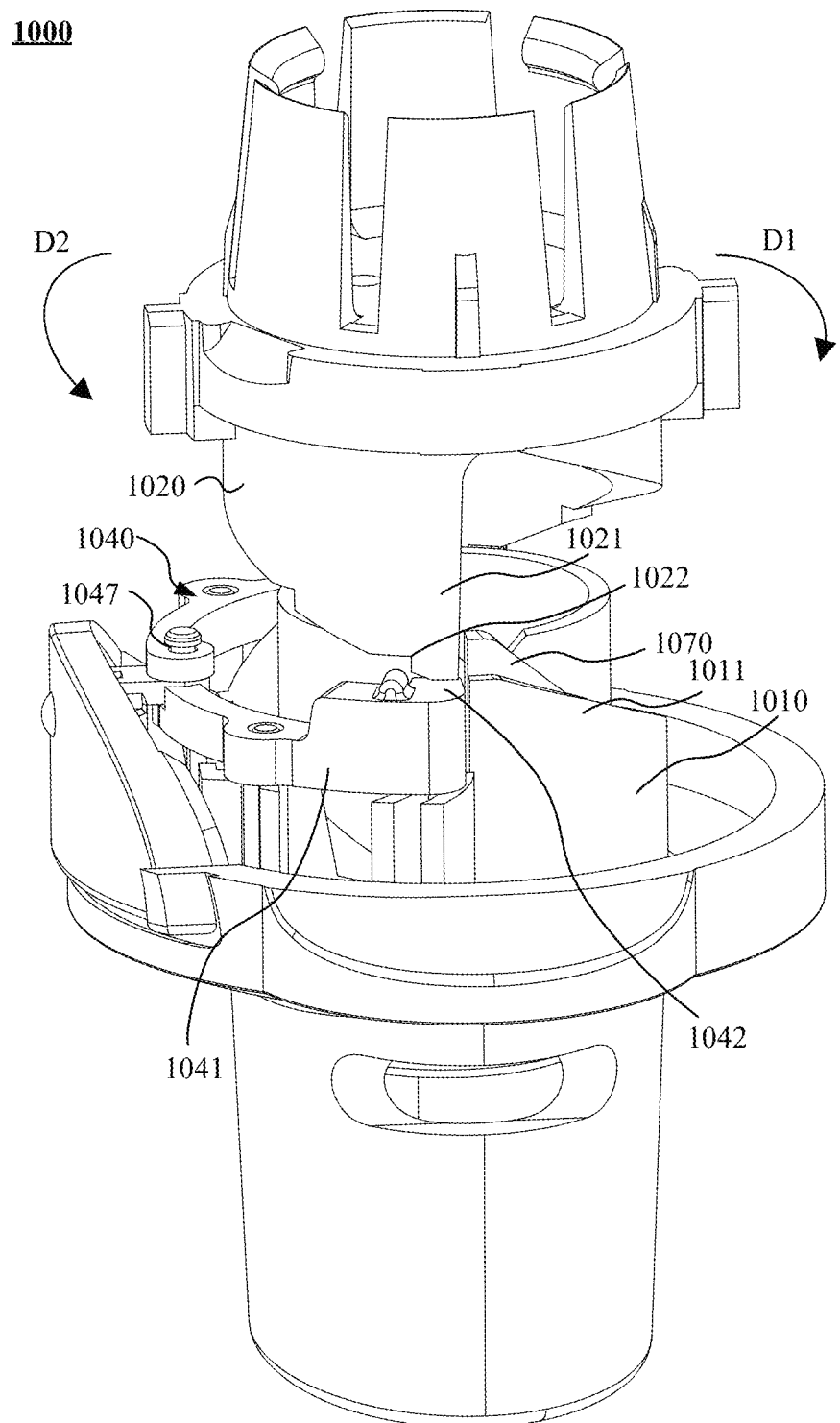
FIG. 5 is another schematic diagram illustrating a trigger assembly for an inhaler in a preloaded position state according to an example embodiment.
Figure 6:
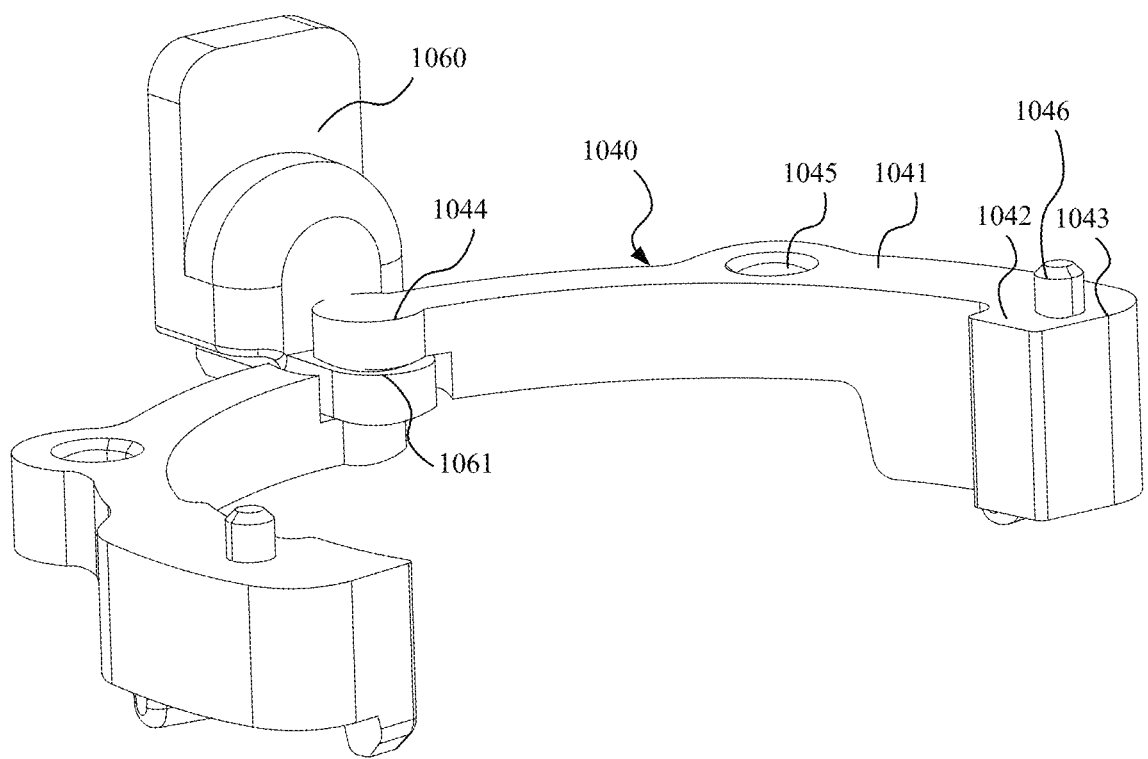
FIG. 6 is a schematic diagram illustrating an actuator and a button connector of a trigger assembly for an inhaler according to an example embodiment.
Figure 7:
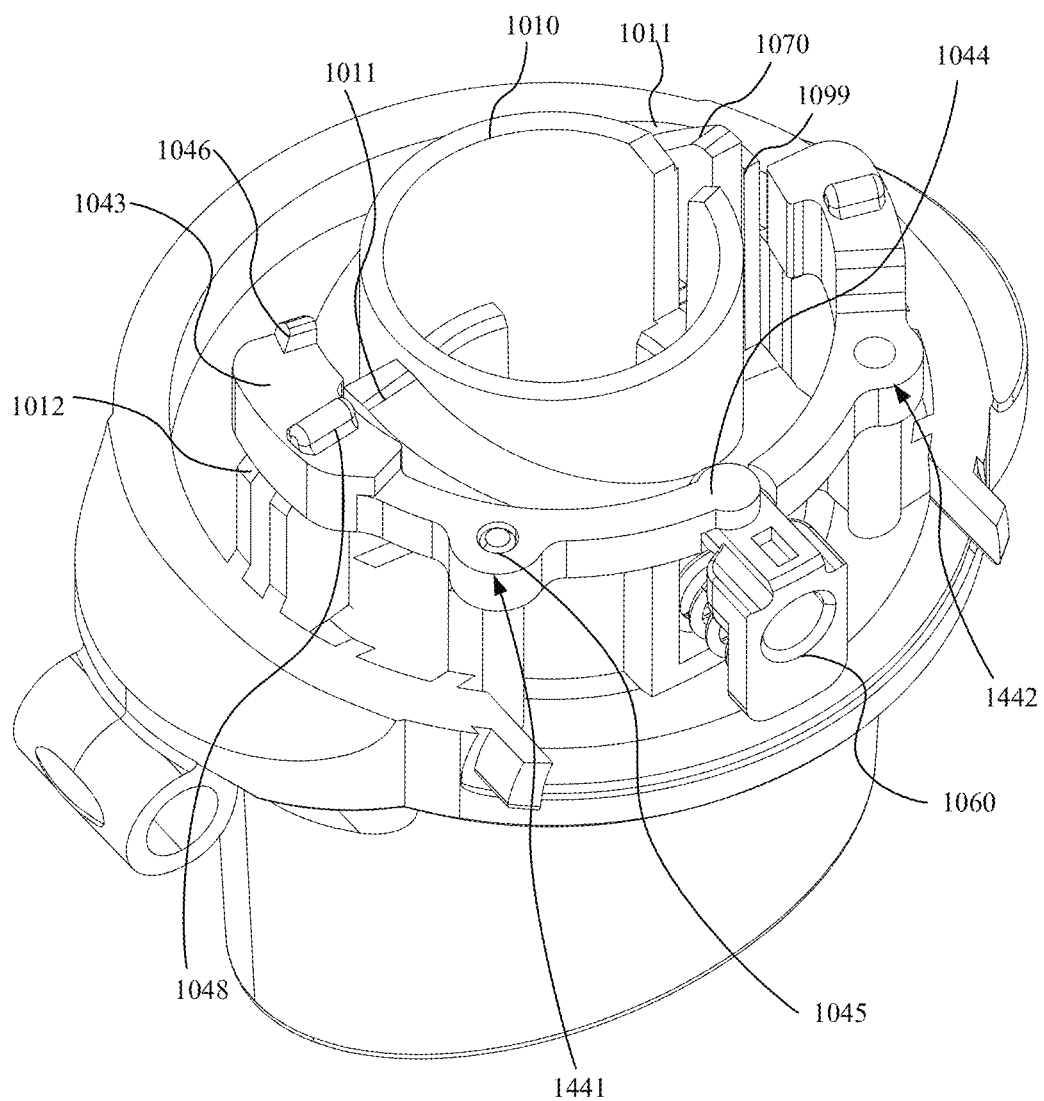
FIG. 7 is a schematic diagram illustrating an actuator and a button connector, which are mounted on a first component, of a trigger assembly for an inhaler according to an example embodiment.

A trigger assembly according to an example embodiment will be described below with reference to FIGS. 1 to 7. In these figures, FIG. 1 is a schematic diagram illustrating a trigger assembly for an inhaler in a triggered position state according to an example embodiment; FIGS. 2 and 3 are schematic diagrams illustrating a trigger assembly for an inhaler in an intermediate state according to an example embodiment; and FIGS. 4 and 5 are schematic diagrams illustrating a trigger assembly for an inhaler in a preloaded position state according to an example embodiment. Moreover, FIG. 6 is a schematic diagram illustrating an actuator and a button connector of a trigger assembly for an inhaler according to an example embodiment; and FIG. 7 is a schematic diagram illustrating an actuator and a button connector, which are mounted on a first component, of a trigger assembly for an inhaler according to an example embodiment.

In the scope of the present disclosure, the "preloaded position" of the trigger assembly may refer to a position where a liquid in the inhaler is loaded to be prepared for outward spraying (e.g., from a reservoir into a pumping chamber). In this position, if there is no triggering action of an external force, the inhaler cannot perform the spraying itself, and only by triggering the trigger assembly, for example, by manually operating (e.g., pressing), the trigger assembly can be restored from the "preloaded position" to the "triggered position", i.e., the liquid in the inhaler is switched from a state in which the liquid is already loaded for pre-spraying, to a state of spraying. In the "triggered position", the inhaler can be operated (e.g., turned) again to the "preloaded position", and therefore the "triggered position" may also be referred to as an initial position.

Figure 11:
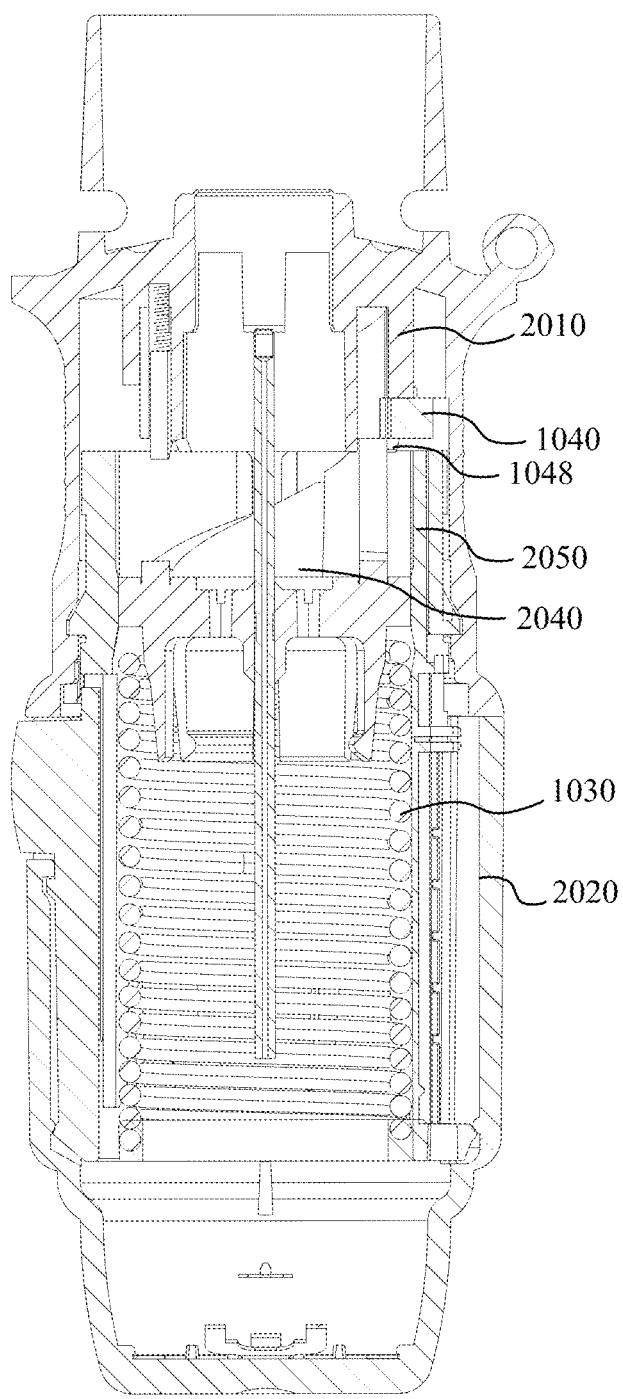
FIG. 11 is a cross-sectional view of the inhaler, along line A-A in FIG. 10, according to an example embodiment.

First, referring to FIGS. 1 to 5 and FIG. 11, a trigger assembly 1000 for an inhaler includes: a first component 1010, a second component 1020, a first elastic member 1030 (the first elastic member 1030 is not shown in FIGS. 1 to 5 for conciseness of the figures, but is shown in FIG. 11) and an actuator 1040.

The second component 1020 in FIG. 1 is in a triggered position (i.e., an initial position), the second component 1020 in FIGS. 4 and 5 is in a preloaded position, and the second component 1020 in FIGS. 2 and 3 is in an intermediate state between the triggered position and the preloaded position. In an example, in the preloaded position, a medical liquid can be pumped from a reservoir into a pumping chamber arranged at the first component 1010 or the second component 1020; and in the triggered position, the medical liquid can be sprayed outward through a spray nozzle from the pumping chamber, and accordingly the second component 1020 in the triggered position is in the initial position of a next action cycle after the spraying is completed and can thus move again to the preloaded position.

The first component 1010 and the second component 1020 are configured such that the second component 1020 is capable of moving away from the first component 1010 to the preloaded position in the case where the second component 1020 rotates relative to the first component 1010 in a first direction D1. For example, referring to FIGS. 1 to 5, starting from the position shown in FIG. 1, the second component 1020 rotates relative to the first component 1010 in a clockwise direction in FIG. 1. As shown in FIGS. 2 and 3, when the second component 1020 rotates, the second component 1020 gradually moves away from the first component 1010; and when the second component 1020 further rotates clockwise, the second component 1020 moves to the preloaded position shown in FIGS. 4 and 5. In an example, a rotational movement between the first component 1010 and the second component 1020 can be converted into a relative movement between the two components by means of a gear and rack mechanism or a screw mechanism.

The first elastic member 1030 is configured to store energy when the second component 1020 moves away from the first component 1010. For example, the first elastic member 1030 may be a spring or other elastic members, as long as energy can be stored by means of elastic deformation. In an example, the first elastic member 1030 (e.g., the spring) may be arranged on a side of the second component 1020 close to the first component 1010, when the second component 1020 moves away from the first component 1010, tensile deformation occurs to store energy, and when the first elastic member 1030 springs back, the second component 1020 can be pushed into the triggered position by means of a tensile force; and in an example shown in FIG. 11, the first elastic member 1030 (e.g., the spring) may be arranged on a side of the second component 1020 away from the first component 1010, when the second component 1020 moves away from the first component 1010, compressive deformation occurs to store energy, and when the first elastic member 1030 springs back, the second component 1020 can be pushed into the triggered position by means of a pushing force.

The actuator 1040 is configured to block the second component 1020 from leaving the preloaded position in the case where the second component 1020 moves to the preloaded position, and configured to, upon being triggered, release the second component 1020 such that the second component 1020 moves to the triggered position toward the first component 1010 under the action of the first elastic member 1030. For example, the actuator 1040 may have a surface for blocking the second component 1020, and a position of the actuator 1040 relative to the second component 1020 can vary with triggering to release the second component 1020. Thus, the reliable switching of the trigger assembly 1000 is achieved between the preloaded position and the triggered position. Accordingly, the use convenience of the inhaler can be improved.

In some embodiments, as shown in FIGS. 1 to 5, the actuator 1040 may be arranged partially around at least one of the first component 1010 or the second component 1020.

For example, the actuator 1040 may be connected to the first component 1010 and arranged partially around a circumference of the first component 1010; or the actuator 1040 may be connected to the second component 1020 and arranged partially around a circumference of the second component 1020; or the actuator 1040 may be connected to the first component 1010 and the second component 1020 and partially arranged around the two components. Referring further to FIGS. 5 and 6, the actuator 1040 includes a bearing portion 1042 extending radially inward from a body 1041 of the actuator 1040. For example, the body 1041 of the actuator 1040 may be in a substantially annular shape such that an inner circumference of the actuator can substantially surround the first component 1010 or the second component 1020 having a substantially cylindrical outer surface. The bearing portion 1042 of the actuator 1040 extends radially from the annular body 1041 toward an annular interior.

It can be seen from FIGS. 1 to 5 that, during the rotation of the second component 1020 relative to the first component 1010, no interference is caused to the rotation of the second component 1020 since the actuator 1040 surrounds the circumference of at least one of the first component 1010 or the second component 1020. Conversely, when the second component 1020 rotates, the actuator 1040 slides relative to an outer circumferential surface of the second component 1020. When the second component 1020 moves to the preloaded position as shown in FIGS. 4 and 5, since the bearing portion 1042 of the actuator 1040 is closer to an inner side relative to the body 1041 in the radial direction, the bearing portion extending inward in the radial direction can abut against the second component 1020 to block the second component 1020 from leaving the preloaded position. For example, an upper surface of the bearing portion 1042 in FIG. 5 abuts against a lower surface of a portion of the second component 1020 to prevent the second component 1020 from further moving downward away from the preloaded position.

In some embodiments, further referring to FIGS. 4 and 5, the actuator 1040 can be configured such that: the second component 1020 can exactly abut against the bearing portion 1042 of the actuator 1040 when the second component 1020 is disengaged from the first component 1010. For example, the actuator 1040 may be constructed as described above by setting the size of the body 1041 of the actuator 1040 (or the position of the bearing portion 1042 of the actuator 1040). In an example, the actuator 1040 may be connected to the first component 1010, and the position of the bearing portion 1042 of the actuator 1040 may be set at a position where the second component 1020 is exactly disengaged from the first component 1010. Thus, when the second component 1020 is disengaged from the first component 1010, the bearing portion 1042 smoothly abuts against the second component 1020 to achieve a smooth transition of the second component 1020 from the intermediate state to a preloaded state, instead of resulting in the splashing of a small amount of liquid due to a non-smooth transition.

In some embodiments, the bearing portion 1042 may be configured to disengage from the second component 1020 to release the second component 1020 upon the actuator 1040 being triggered. For example, the actuator 1040 may be constructed as described above by setting the size of the bearing portion 1042 of the actuator 1040. In an example, continuing to refer to FIGS. 1 to 5, an inward extending distance of the bearing portion 1042 may not necessarily be excessively large as long as the requirement for abutting against the second component 1020 can be met. In this way, when it is required to switch the second component 1020 from the preloaded position to the triggered position, the second component 1020 can be released only by slightly moving the position of the bearing portion 1042 (e.g., slightly moving outward the bearing portion 104 in the radial direction in FIG. 5).

In some embodiments, as shown in FIG. 4, the trigger assembly 1000 may further include a second elastic member 1050, the second elastic member 1050 is mechanically coupled to the actuator 1040, and when the second component 1020 moves to the preloaded position, the actuator 1040 moves, under the action of the second elastic member 1050, to a position where the bearing portion 1042 of the actuator abuts against the second component 1020.

For example, the second elastic member 1050 may be a spring or other elastic members as long as energy can be stored by means of elastic deformation. In an example, the second elastic member 1050 (e.g., a spring) may be directly or indirectly connected to the actuator 1040 as long as the second elastic member can be compressed or stretched to deform by the actuator 1040, and can force the actuator 1040, upon being triggered, to move to a position where the bearing portion 1042 of the actuator abuts against the second component 1020, by means of an elastic force. In an example, the second elastic member 1050 may be arranged inside the first component 1010.

In some embodiments, as shown in FIGS. 2 and 3, before the second component 1020 moves to the preloaded position, the actuator 1040 leans against a side wall of the second component 1020 under the action of the second elastic member 1050. Thus, once the second component 1020 moves to the preloaded position, the actuator 1040 leaning against an inner wall thereof can further rapidly move inward in the radial direction to allow the bearing portion 1042 to abut against the second elastic member 1050.

In some embodiments, as shown in FIG. 4, one end of the second elastic member 1050 is coupled to the actuator 1040 by means of a button connector 1060, and the other end of the second elastic member 1050 abuts against the first component 1010. For example, the first component 1010 may be internally provided with a groove for accommodating the second elastic member 1050, and the second elastic member 1050 is arranged between the button connector 1060 and the groove. Moreover, the button connector 1060 may be, for example, connected to a button of the inhaler (the button of the inhaler in FIG. 5 covers the button connector), and a user may press, for example, by pressing the button, the button connector 1060 to operate the actuator 1040. As shown in FIG. 6, the button connector 1060 may be provided with a connecting slot 1061, the actuator 1040 may be provided with a connecting rod 1047 (shown in FIG. 5) inserted into the connecting slot, and the connecting rod may be pivoted in the connecting slot.

In some embodiments, continuing to refer to FIG. 6, the actuator 1040 may be configured in the shape of a curved arm, the curved arm being arranged around at least one of the first component 1010 or the second component 1020, and a first end 1043 of the curved arm (i.e., an end away from the button connector 1060 in FIG. 6) is configured to block the second component 1020 from leaving the preloaded position.

In some embodiments, continuing to refer to FIG. 6, a second end 1044 of the actuator 1040 opposite to the first end 1043 is movably connected to the button connector 1060, and a connecting portion 1045 between the first end 1043 and the second end 1044 of the actuator 1040 can be pivotally connected to at least one of the first component 1010 or the second component 1020, such that the actuator 1040 is capable of pivoting around the connecting portion 1045 by operating the button connector 1060. For example, in FIG. 7, the second component is hidden, it can be seen that the second end 1044 is movably connected to the button connector 1060, and the connecting portion 1045 can be pivotally connected to a shaft on the first component 1010, such that when the user presses the button connector 1060 by pressing the button, the second end 1044 of the actuator 1040 moves inward (toward the first component 1010) in the radial direction to allow the actuator 1040 in the shape of the curved arm to rotate around its own connecting portion 1045, and thus the first end 1043 moves outward (away from the first component 1010) in the radial direction.

The connecting portion 1045 of the actuator 1040 may also be pivotally connected to the second component 1020, which will not be described in detail herein.

In some embodiments, the first component 1010 may include a first helical portion 1011, the second component 1020 may include a second helical portion 1021, and a helical end surface of the second helical portion 1021 can mate with a helical end surface of the first helical portion 1011. In addition, the first helical portion 1011 and the second helical portion 1021 are configured to be movable to the preloaded position in the case where the second component 1020 rotates relative to the first component 1010 in the first direction D1 (e.g., the clockwise direction in FIGS. 1 to 5) along the mating first and second helical portions 1011 and 1021. In other words, the helical end surfaces of the first helical portion 1011 and the second helical portion 1021 can be combined together, for example, a higher part of one of the first and second helical portions can be combined with a lower part of the other helical portion, the two parts can achieve relative rotation, and during the relative rotation (e.g., from FIGS. 1 to 3 and then to FIG. 5), the second helical portion 1021 can gradually move away from the first component 1010 due to the spiral end surfaces and thus gradually reach the preloaded position.

In some embodiments, referring to FIG. 4 or 5, at least one of the first helical portion 1011 or the second helical portion 1021 may be configured such that the second helical portion 1021 is disengaged from the first helical portion 1011 in the case where the second component 1020 moves to the preloaded position. The disengagement of the second helical portion 1021 from the first helical portion 1011 means that no contact occurs between the two helical portions, so that when released, the second component 1020 smoothly returns to the initial position, that is, the triggered position.

In some embodiments, the actuator 1040 may be configured to abut against the second helical portion 1021 to block the second component 1020 from leaving the preloaded position when the second helical portion 1021 is disengaging from the first helical portion 1011. Continuing to refer to FIG. 4 or 5, it can be seen that the second helical portion 1021 has now been disengaged from the first helical portion 1011. In this example, the liquid in the inhaler has been loaded and is in the preloaded state. In order to maintain the trigger assembly 1000 in the preloaded state, the actuator 1040 (e.g., the bearing portion 1042 of the actuator 1040) abuts against the second helical portion 1021, which has been disengaged from the first helical portion 1011.

In some embodiments, referring to FIG. 1, in the case where the second component 1020 moves to the triggered position (the initial position), the helical end surface of the second helical portion 1021 (as shown in FIG. 5) is attached to the helical end surface of the first helical portion 1011 (as shown in FIG. 5). After the actuator 1040 is triggered, the actuator 1040 stops abutting against the second helical portion 1021 of the second component 1020, the second component 1020 can return to the triggered position (the initial position) under the action of the first elastic member 1030, and in this case, the helical end surface of the second helical portion 1021 is attached to the helical end surface of the first helical portion 1011 to form a relatively complete cylindrical shape, thus reducing space occupancy.

In some embodiments, the first helical portion includes two centrally symmetrical first helical portions 1011, and the second helical portion includes two centrally symmetrical second helical portions 1021. Also, the actuator 1040 includes a first actuator 1441 and a second actuator 1442 arranged on two circumferential sides of at least one of the first component 1010 or the second component 1020, and the first actuator 1441 and the second actuator 1442 are respectively configured to abut against a respective one of the two second helical portions. As shown in FIG. 7, the first actuator 1441 and the second actuator 1442 are respectively arranged on the two circumferential sides of the first component 1010, the first actuator 1441 and the second actuator 1442 can respectively bear two second helical portions 1021 when the second component 1020 is in the preloaded position, and thus the bearing stability of the second component 1020 can be improved.

In some embodiments, as shown in FIG. 6, the actuator 1040 may include a limiting protrusion 1046, and the limiting protrusion 1046 is arranged adjacent to the bearing portion 1042 and protrudes from a bearing surface of the bearing portion 1042. The limiting protrusion 1046 is configured to block the rotation of the second component 1020 in the first direction D1 in the case where the bearing portion 1042 abuts against the second helical portion 1021. As shown in FIG. 4, in this case, when the second component 1020 is in the preloaded position, the bearing portion 1042 abuts against the second helical portion 1021, the limiting protrusion 1046 blocks the rotation of the second component 1020 in the first direction D1 (the clockwise direction in FIG. 4), and thus an unexpected rotation in the first direction D1 can be prevented from occurring between the second component 1020 and the first component 1010.

In some embodiments, a limiting step 1022 is arranged at an end of the second helical portion 1021 of the second component 1020, and the limiting protrusion 1046 of the actuator 1040 blocks the rotation of the second component 1020 in the first direction D1 by abutting against the limiting step 1022.

In some embodiments, the trigger assembly 1000 may further include a backstop member 1070, which is retractably arranged in the first component 1010 to block the rotation of the second component 1020 in a second direction D2 opposite to the first direction D1 in the case where the second component 1020 moves to the preloaded position. Referring first to FIG. 5, when the second component 1020 is in the preloaded position, the backstop member 1070 is in a state where the backstop member extends out of the first component 1010 and is thus higher than the highest point of the first component 1010. Thus, the backstop member can block the rotation of the second component 1020 in the second direction D2 (the counterclockwise direction in FIG. 5) opposite to the first direction D1. Referring next to FIG. 3, when the second component 1020 further rotates in the first direction D1 (the clockwise direction) relative to the first component 1010, the backstop member 1070 is in a state where the backstop member retracts back to the first component 1010 and therefore does not affect the rotation of the second component 1020 in the first direction D1.

Figure 8:
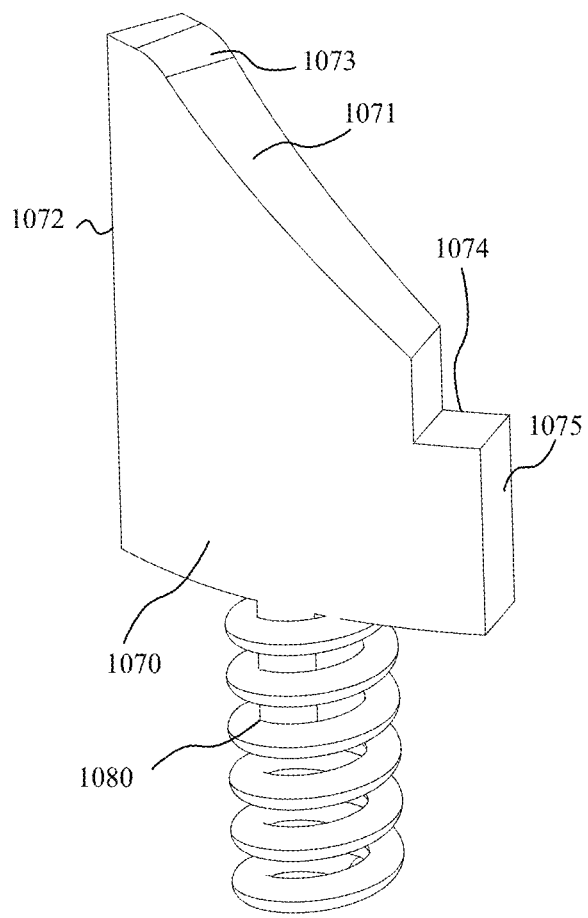
FIG. 8 is a schematic diagram illustrating a backstop member of a trigger assembly for an inhaler according to an example embodiment.
Figure 9:
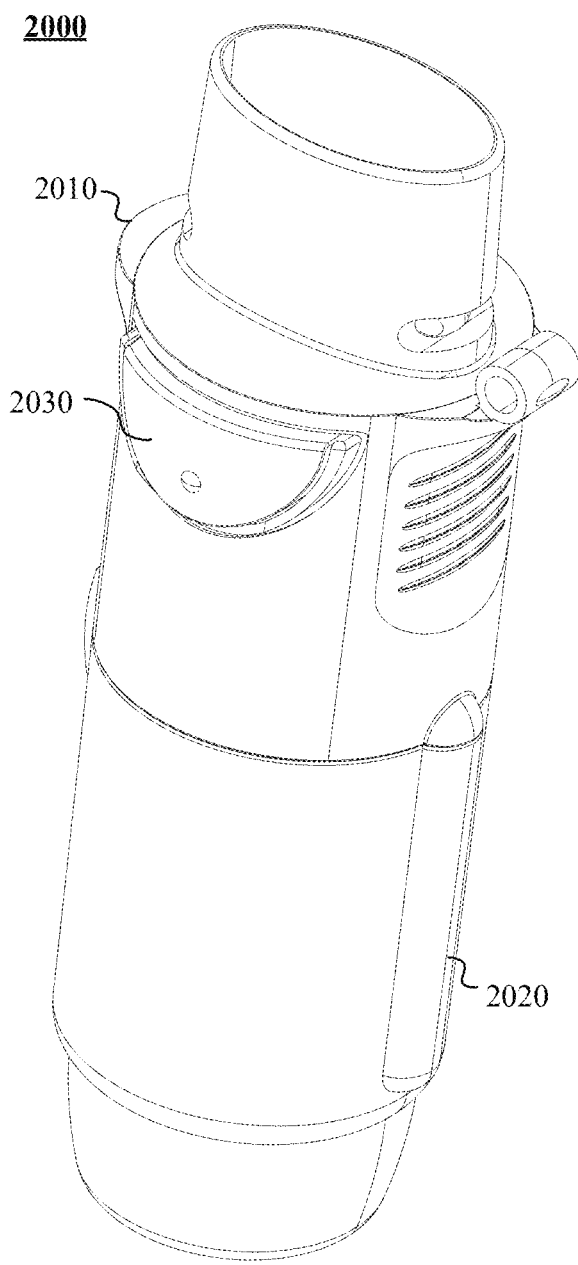
FIG. 9 is a perspective view illustrating an inhaler according to an example embodiment.
Figure 10:
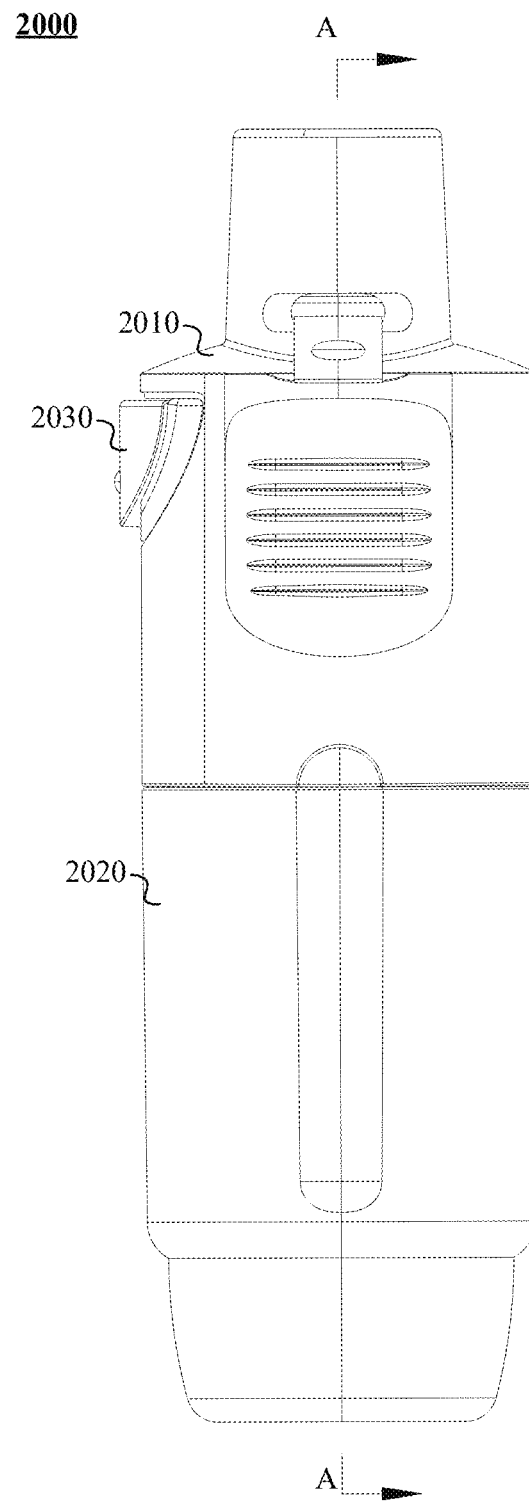
FIG. 10 is a side view illustrating an inhaler according to an example embodiment.

Referring to FIG. 8, FIG. 8 is a schematic diagram illustrating the backstop member of the trigger assembly for the inhaler according to an example embodiment. In some embodiments, the backstop member 1070 may include a beveled portion 1071, and the beveled portion 1071 is configured to allow the backstop member 1070 to at least partially retract into the first component 1010 under the pressing action of the second component 1020. For example, the beveled portion 1071 may substantially match the helical end surface of the second helical portion 1021 of the second component 1020, and the beveled portion 1071 may also have a substantially helical end surface. The backstop member 1070 at least partially retracts back to the first component 1010 as long as the backstop member 1070 does not block the rotation of the second component 1020 in the first direction D1.

In some embodiments, the backstop member 1070 may be configured such that: during the disengagement of the second component 1020 from the preloaded position, the backstop member 1070 extends at least partially out of the first component 1010, such that a straight portion 1072 of the backstop member 1070 opposite to the beveled portion 1071 can block the rotation of the second component 1020 in the second direction D2. For example, when the second component 1020 is switched from the position shown in FIG. 3 to the position shown in FIG. 5, the backstop member 1070 extends at least partially out of the first component 1010, such that the straight portion 1072 thereof blocks the rotation of the second component 1020 in the second direction D2 (the counterclockwise direction).

In some embodiments, as shown in FIG. 8, the trigger assembly 1000 may further include a backstop elastic member 1080, and the first component 1010 may further include a groove 1099 for receiving the backstop member 1070. Furthermore, the backstop elastic member 1080 is arranged between the backstop member 1070 and the groove 1099 to provide the backstop member 1070 with an elastic force allowing the backstop member to protrude from the groove 1099. When the second component 1020 stops pressing the backstop member 1070, the backstop member 1070 can protrude from the first component 1010 under the action of the elastic force of the backstop elastic member 1080 to block the rotation of the second component 1020 in the second direction D2.

In some embodiments, further referring to FIG. 8, the backstop member 1070 may include a beveled chamfer 1073, and the beveled chamfer 1073 may be arranged at a first end of the beveled portion 1071. In the process of the second component 1020 rotating and downwardly pressing the backstop member 1070, the first end of the beveled portion 1071 finally comes into contact with the second component 1020 relative to other parts of the beveled portion 1071. Thus, the beveled chamfer 1073 is conducive to a smooth transition when the second component 1020 leaves the backstop member 1070, thereby reducing jerking.

In some embodiments, further referring to FIG. 8, the backstop member 1070 may include a step portion 1074, and the step portion 1074 may be arranged at a second end of the beveled portion 1071. In the process of the second component 1020 rotating and downwardly pressing the backstop member 1070, a second end of the beveled portion 1071 firstly comes into contact with the second component 1020 relative to other parts of the beveled portion 1071. Therefore, the step portion 1074 is conducive to preventing a side edge 1075 of the backstop member 1070 from unexpectedly blocking the second component due to an excessively large height, and accordingly a certain mounting tolerance is provided for the amount of extension of the backstop member 1070 out of the first component 1010.

Further, some inhalers are still inconvenient to operate, and misoperations are very possible to occur especially if the user needs multiple operations to complete spraying. For example, the user likely performs an unexpectedly reverse or excessive rotation on the inhaler when the inhaler is set to complete spraying by means of a rotation operation by the user. These misoperations possibly cause the interference of components in the inhaler or inaccurate atomization doses.

In view of this, by providing the retractable backstop member, an unexpected reverse rotation of the second component can be prevented in the case where the second component has been moved to the preloaded position. Referring to FIGS. 1 to 5, FIG. 8 and FIG. 11, the trigger assembly 1000 for the inhaler includes: the first component 1010, the second component 1020, the actuator 1040 and the backstop member 1070. It can be seen that the second component 1020 in FIG. 1 is in the triggered position (i.e., the initial position), the second component 1020 in FIGS. 4 and 5 is in the preloaded position, and the second component 1020 in FIGS. 2 and 3 is in the intermediate state between the triggered position and the preloaded position. In an example, in the preloaded position, a medical liquid can be pumped from the reservoir into the pumping chamber arranged at the first component 1010 or the second component 1020; and in the triggered position, the medical liquid can be sprayed outward through the spray nozzle from the pumping chamber, and accordingly the second component 1020 in the triggered position is in the initial position of a next action cycle after the spraying is completed and can thus move again to the preloaded position.

The first component 1010 and the second component 1020 are configured such that the second component 1020 is capable of moving away from the first component 1010 to the preloaded position in the case where the second component rotates relative to the first component 1010 in the first direction D1. For example, referring to FIGS. 1 to 5, starting from the position shown in FIG. 1, the second component 1020 rotates relative to the first component 1010 in the clockwise direction in FIG. 1. As shown in FIGS. 2 and 3, when the second component 1020 rotates, the second component 1020 gradually moves away from the first component 1010; and when the second component 1020 further rotates clockwise, the second component 1020 moves to the preloaded position shown in FIGS. 4 and 5. In an example, the rotational movement between the first component 1010 and the second component 1020 can be converted into the relative movement between the two components by means of the gear and rack mechanism or the screw mechanism.

The actuator 1040 is configured to release the second component 1020 such that the second component 1020 moves toward the first component 1010 from the preloaded position to the triggered position.

The backstop member 1070 can be retractably arranged in the first component 1010 to block the rotation of the second component 1020 in the second direction D2 opposite to the first direction D1 in the case where the second component 1020 moves to the preloaded position. Referring first to FIG. 5, when the second component 1020 is in the preloaded position, the backstop member 1070 is in the state where the backstop member extends out of the first component 1010 and is thus higher than the highest point of the first component 1010. Thus, the backstop member can block the rotation of the second component 1020 in the second direction D2 (the counterclockwise direction in FIG. 5) opposite to the first direction D1. Referring next to FIG. 3, when the second component 1020 further rotates in the first direction D1 (the clockwise direction) relative to the first component 1010, the backstop member 1070 is in the state where the backstop member retracts back to the first component 1010 and therefore does not affect the rotation of the second component 1020 in the first direction D1. Thus, the unexpected reverse rotation of the second component 1020 can be blocked in the case where the second component 1020 moves to the preloaded position.

In a second aspect, the present disclosure provides an inhaler. The inhaler includes the trigger assembly 1000 of the present disclosure, and the trigger assembly 1000 is configured to trigger the inhaler to spray atomized fluid.

The inhaler of the present disclosure will be further described below in conjunction with FIGS. 9 to 11. FIG. 9 is a perspective view illustrating an inhaler according to an example embodiment; FIG. 10 is a side view illustrating an inhaler according to an example embodiment; and FIG. 11 is a cross-sectional view of the inhaler, along line A-A in FIG. 10, according to an example embodiment.

As shown in FIGS. 9 to 11, the inhaler 2000 may include an upper housing 2010, a lower housing 2020, a button 2030 arranged in the upper housing, and a delivery tube socket 2040 arranged in the lower housing 2020.

In some embodiments, the first component 1010 may be constructed as the upper housing 2010 of the inhaler 2000, the second component 1020 may be constructed as the delivery tube socket 2040 of the inhaler 2000, and the delivery tube socket 2040 is configured to rotate as the lower housing 2020 of the inhaler 2000 rotates. For example, the upper housing 2010 and the lower housing 2020 may be rotated relative to each other, and the delivery tube socket 2040 is coupled to the lower housing 2020. By rotating the lower housing 2020 relative to the upper housing 2010, the delivery tube socket 2040 can rotate relative to the upper housing 2010, in other words, by rotating the lower housing 2020 relative to the upper housing 2010, the second component 1020 of the trigger assembly 1000 arranged in the inhaler 2000 can rotate relative to the first component 1010, and the second component 1020 moves away from the first component 1010 to the preloaded position. In this process, a part of the liquid stored in the reservoir of the inhaler 2000 may be pumped, for example, into the pumping chamber of the inhaler 2000 to prepare for spraying.

In some embodiments, when the user presses the button 2030, the button 2030 may trigger the actuator 1040 by means of, for example, the button connector 1060, and thus the actuator 1040 can release the delivery tube socket 2040 to move the delivery tube socket 2040 to the triggered position toward the upper housing 2010 under the action of the first elastic member 1030. In this process, the volume of the pumping chamber is reduced under the pressing action of the delivery tube socket 2040, and a pressure in the pumping chamber is increased, such that the liquid inside the pumping chamber is atomized and sprayed through an outlet above the upper housing 2010.

Thus, the use convenience of the inhaler is improved.

In some embodiments, the inhaler 2000 may include a main rotating body 2050, and the main rotating body 2050 is located inside the lower housing 2020 and is arranged outside the delivery tube socket 2040. The main rotating body 2050 can transfer the rotation of the lower housing 2020 to the delivery tube socket 2040, in other words, as the main rotating body 2050 rotates, the delivery tube socket 2040 also rotates accordingly; in addition, when the delivery tube socket 2040 is released to move toward the upper housing 2010, the main rotating body 2050 does not move up along with the delivery tube socket 2040.

In an example, both the upper housing 2010 and the main rotating body 2050 can be used to longitudinally position the actuator 1040. For example, referring to FIG. 7, one end surface of the actuator may abut against a ribbed plate 1012 of the first component 1010. Returning to FIG. 11, it can correspondingly be seen that a lower end surface of the ribbed plate of the upper housing 2010 abuts against an upper end surface of the actuator 1040. In addition, referring again to FIG. 7, the actuator may be provided with a longitudinal positioning protrusion 1048, and returning to FIG. 11, it can correspondingly be seen that an upper end surface of a part of the main rotating body 2050 can abut against a lower end surface of the longitudinal positioning protrusion 1048 of the actuator 1040. Thus, both the upper housing 2010 and the main rotating body 2050 can longitudinally position the actuator 1040.

Some example items of the present disclosure will be described below.

Item 1. A trigger assembly for an inhaler, including: a first component; a second component, where the first component and the second component are configured such that the second component is capable of moving away from the first component to a preloaded position in the case where the second component rotates relative to the first component in a first direction; a first elastic member, which is configured to store energy when the second component moves away from the first component; and an actuator, which is configured to block the second component from leaving the preloaded position in the case where the second component has been moved to the preloaded position, and configured to, upon being triggered, release the second component such that the second component moves to a triggered position toward the first component under the action of the first elastic member.

Item 2. The trigger assembly according to item 1, where the actuator is arranged partially around at least one of the first component or the second component, the actuator includes a bearing portion extending radially inward from a body of the actuator, and the bearing portion is configured to abut against the second component to block the second component from leaving the preloaded position.

Item 3. The trigger assembly according to item 2, where the actuator is configured such that: the second component abuts against the bearing portion of the actuator when the second component is disengaged from the first component.

Item 4. The trigger assembly according to item 2, where the bearing portion is configured to disengage from the second component to release the second component upon the actuator being triggered.

Item 5. The trigger assembly according to item 2, further including a second elastic member, the second elastic member being coupled to the actuator, where when the second component has been moved to the preloaded position, the actuator moves, under the action of the second elastic member, to a position where the bearing portion thereof abuts against the second component.

Item 6. The trigger assembly according to item 5, where before the second component has been moved to the preloaded position, the actuator leans against a side wall of the second component under the action of the second elastic member.

Item 7. The trigger assembly according to item 5, further including a button connector, where one end of the second elastic member is coupled to the actuator by means of the button connector, and the other end of the second elastic member abuts against the first component.

Item 8. The trigger assembly according to any one of items 1 to 7, where the actuator is configured to be in the shape of a curved arm, the curved arm being arranged around at least one of the first component or the second component, and where a first end of the curved arm is configured to block the second component from leaving the preloaded position.

Item 9. The trigger assembly according to item 8, further including a button connector, where a second end of the actuator opposite to the first end is movably connected to the button connector, and where a connecting portion between the first end and the second end of the actuator is pivotably connected to at least one of the first component or the second component, such that the actuator is capable of pivoting around the connecting portion by operating the button connector.

Item 10. The trigger assembly according to item 2, where the first component includes a first helical portion, and the second component includes a second helical portion, a helical end surface of the second helical portion being capable of mating with a helical end surface of the first helical portion; and where the first and second helical portions are configured to be movable to the preloaded position in the case where the second component rotates relative to the first component along the mating first and second helical portions.

Item 11. The trigger assembly according to item 10, where at least one of the first helical portion or the second helical portion is configured such that: the second helical portion is disengaged from the first helical portion in the case where the second component has been moved to the preloaded position.

Item 12. The trigger assembly according to item 11, where the actuator is configured to abut against the second helical portion to block the second component from leaving the preloaded position when the second helical portion is disengaging from the first helical portion.

Item 13. The trigger assembly according to item 10, where the helical end surface of the second helical portion is attached to the helical end surface of the first helical portion in the case where the second component has been moved to the triggered position.

Item 14. The trigger assembly according to item 10, where the first helical portion includes two centrally symmetrical first helical portions, and the second helical portion includes two centrally symmetrical second helical portions; and where the actuator includes a first actuator and a second actuator arranged on two circumferential sides of at least one of the first component or the second component, and the first actuator and the second actuator are respectively configured to abut against a respective one of the two second helical portions.

Item 15. The trigger assembly according to item 10, where the actuator includes a limiting protrusion, the limiting protrusion is arranged adjacent to the bearing portion and protrudes from a bearing surface of the bearing portion, and the limiting protrusion is configured to block the rotation of the second component in the first direction in the case where the bearing portion abuts against the second helical portion.

Item 16. The trigger assembly according to item 15, where a limiting step is arranged at an end of the second helical portion of the second component, and the limiting protrusion of the actuator blocks the rotation of the second component in the first direction by abutting against the limiting step.

Item 17. The trigger assembly according to any one of items 1 to 7, further including a backstop member, which is retractably arranged in the first component to block the rotation of the second component in a second direction opposite to the first direction in the case where the second component has been moved to the preloaded position.

Item 18. The trigger assembly according to item 17, where the backstop member includes a beveled portion configured to allow the backstop member to at least partially retract into the first component under the pressing action of the second component.

Item 19. The trigger assembly according to item 18, where the backstop member is configured to protrude partially from the first component during the movement of the second component to the preloaded position, such that a straight portion of the backstop member opposite to the beveled portion is capable of blocking the rotation of the second component in the second direction.

Item 20. The trigger assembly according to item 17, further including a backstop elastic member, where the first component includes a groove for receiving the backstop member, and where the backstop elastic member is arranged between the backstop member and the groove to provide the backstop member with an elastic force allowing the backstop member to protrude from the groove.

Item 21. A trigger assembly for an inhaler, including: a first component; a second component, where the first component and the second component are configured such that the second component is capable of moving away from the first component to a preloaded position in the case where the second component rotates relative to the first component in a first direction; a backstop member, which is retractably arranged in the first component to block the rotation of the second component in a second direction opposite to the first direction in the case where the second component has been moved to the preloaded position; and an actuator, the actuator being configured to release the second component such that the second component moves toward the first component from the preloaded position to a triggered position.

Item 22. The trigger assembly according to item 21, further including a first elastic member configured to store energy when the second component moves away from the first component, where the actuator is configured to block the second component from leaving the preloaded position in the case where the second component has been moved to the preloaded position, and configured to, upon being triggered, release the second component such that the second component moves to the triggered position toward the first component under the action of the first elastic member.

Item 23. The trigger assembly according to item 21 or 22, where the backstop member includes a beveled portion, and the beveled portion is configured to allow the backstop member to at least partially retract into the first component under the pressing action of the second component.

Item 24. The trigger assembly according to item 23, where the backstop member is configured to: extend partially out of the first component during the movement of the second component to the preloaded position, such that a straight portion of the backstop member opposite to the beveled portion can block the rotation of the second component in the second direction.

Item 25. The trigger assembly according to item 23, further including a backstop elastic member, where the first component includes a groove for receiving the backstop member, and where the backstop elastic member is arranged between the backstop member and the groove to provide the backstop member with an elastic force allowing the backstop member to protrude from the groove.

Item 26. The trigger assembly according to item 23, where the backstop member includes a beveled chamfer, and the beveled chamfer is arranged at a first end of the beveled portion that last contacts the second component.

Item 27. The trigger assembly according to item 23, where the backstop member includes a step portion, and the step portion is arranged at a second end of the beveled portion that first contacts the second component.

Item 28. The trigger assembly according to item 21 or 22, where the actuator is arranged partially around at least one of the first component or the second component, the actuator includes a bearing portion extending radially inward from a body of the actuator, and the bearing portion is configured to abut against the second component to block the second component from leaving the preloaded position.

Item 29. The trigger assembly according to claim 28, where the actuator includes a limiting protrusion, the limiting protrusion is arranged adjacent to the bearing portion and protrudes from a bearing surface of the bearing portion, and the limiting protrusion is configured to block the rotation of the second component in the first direction in the case where the bearing portion abuts against the second component.

Item 30. The trigger assembly according to claim 29, where the second component is provided with a limiting step, and the limiting protrusion of the actuator blocks the rotation of the second component in the first direction by abutting against the limiting step.

Item 31. The trigger assembly according to item 21 or 22, where the actuator is configured to be in the shape of a curved arm, the curved arm being arranged around at least one of the first component or the second component, and where a first end of the curved arm is configured to block the second component from leaving the preloaded position.

Item 32. The trigger assembly according to item 31, where the actuator includes a limiting protrusion, and the limiting protrusion extends from the first end of the curved arm and is configured to block the rotation of the second component in the first direction in the case where the second component has been moved to the preloaded position.

Item 33. The trigger assembly according to item 31, further including a button connector, where a second end of the actuator opposite to the first end is movably connected to the button connector, and where a connecting portion between the first end and the second end of the actuator is pivotably connected to at least one of the first component or the second component, such that the actuator is capable of pivoting around the connecting portion by operating the button connector.

Item 34. The trigger assembly according to item 21 or 22, where the first component includes a first helical portion, and the second component includes a second helical portion, a helical end surface of the second helical portion being capable of mating with a helical end surface of the first helical portion; and where the first and second helical portions are configured to be movable to the preloaded position in the case where the second component rotates relative to the first component in the first direction along the mating first and second helical portions.

Item 35. The trigger assembly according to item 34, where at least one of the first helical portion or the second helical portion is configured such that the second helical portion is disengaged from the first helical portion in the case where the second component has been moved to the preloaded position.

Item 36. The trigger assembly according to item 35, where the actuator is configured to abut against the second helical portion to block the second component from leaving the preloaded position when the second helical portion is disengaging from the first helical portion.

Item 37. The trigger assembly according to item 28, where the bearing portion is configured to disengage from the second component to release the second component upon the actuator being triggered.

Item 38. The trigger assembly according to item 28, further including a second elastic member, the second elastic member being coupled to the actuator, where when the second component has been moved to the preloaded position, the actuator moves, under the action of the second elastic member, to a position where the bearing portion thereof abuts against the second component.

Item 39. The trigger assembly according to item 34, where the helical end surface of the second helical portion is attached to the helical end surface of the first helical portion in the case where the second component has been moved to the triggered position.

Item 40. The trigger assembly according to item 34, where the first helical portion includes two centrally symmetrical first helical portions, and the second helical portion includes two centrally symmetrical second helical portions; and where the actuator includes a first actuator and a second actuator arranged on two circumferential sides of at least one of the first component or the second component, and the first actuator and the second actuator are respectively configured to abut against a respective one of the two second helical portions.

Item 41. An inhaler, including a trigger assembly according to any one of items 1 to 40, the trigger assembly being configured to trigger the inhaler to spray atomized fluid.

Item 42. The inhaler according to item 41, where the first component is constructed as an upper housing of the inhaler, the second component is constructed as a delivery tube socket of the inhaler, and where the delivery tube socket is configured to be rotatable with rotation of a lower housing of the inhaler.

What is claimed is:

1. A trigger assembly for an inhaler, comprising:
   a first component;
   a second component, wherein the first component and the second component are configured such that the second component is capable of moving away from the first component to a preloaded position in the case where the second component rotates relative to the first component in a first direction; and
   a backstop member, which is retractably arranged in the first component to block the rotation of the second component in a second direction opposite to the first direction in the case where the second component has been moved to the preloaded position, wherein the second component is capable of moving from the preloaded position towards the first component to a triggered position.

2. The trigger assembly according to claim 1, further comprising a first elastic member and an actuator, wherein the first elastic member is configured to store energy when the second component moves away from the first component, and wherein the actuator is configured to block the second component from leaving the preloaded position in the case where the second component has been moved to the preloaded position, and configured to, upon being triggered, release the second component such that the second component moves to a triggered position toward the first component under an action of the first elastic member.

3. The trigger assembly according to claim 1, wherein the backstop member comprises a beveled portion configured to allow the backstop member to at least partially retract into the first component under a pressing action of the second component.

4. The trigger assembly according to claim 3, wherein the backstop member is configured to protrude partially from the first component during the movement of the second component to the preloaded position, such that a straight portion of the backstop member opposite to the beveled portion is capable of blocking the rotation of the second component in the second direction.

5. The trigger assembly according to claim 3, further comprising a backstop elastic member, wherein the first component comprises a groove for receiving the backstop member, and wherein the backstop elastic member is arranged between the backstop member and the groove, to provide the backstop member with an elastic force allowing the backstop member to protrude from the groove.

6. The trigger assembly according to claim 3, wherein the backstop member comprises a beveled chamfer, and the beveled chamfer is arranged at a first end of the beveled portion that last contacts the second component.

7. The trigger assembly according to claim 3, wherein the backstop member comprises a step portion, and the step portion is arranged at a second end of the beveled portion that first contacts the second component.

8. The trigger assembly according to claim 2, wherein the actuator is arranged partially around at least one of the first component or the second component, the actuator comprises a bearing portion extending radially inward from a body of the actuator, and the bearing portion is configured to abut against the second component to block the second component from leaving the preloaded position.

9. The trigger assembly according to claim 8, wherein the actuator comprises a limiting protrusion, the limiting protrusion is arranged adjacent to the bearing portion and protrudes from a bearing surface of the bearing portion, and the limiting protrusion is configured to block the rotation of the second component in the first direction in the case where the bearing portion abuts against the second component.

10. The trigger assembly according to claim 9, wherein the second component is provided with a limiting step, and the limiting protrusion of the actuator blocks the rotation of the second component in the first direction by abutting against the limiting step.

11. The trigger assembly according to claim 2, wherein the actuator is configured in the shape of a curved arm, the curved arm being arranged around at least one of the first component or the second component, and wherein a first end of the curved arm is configured to block the second component from leaving the preloaded position.

12. The trigger assembly according to claim 11, wherein the actuator comprises a limiting protrusion, and the limiting protrusion extends from the first end of the curved arm and is configured to block the rotation of the second component in the first direction in the case where the second component has been moved to the preloaded position.

13. The trigger assembly according to claim 11, further comprising a button connector, wherein a second end of the actuator opposite to the first end is movably connected to the button connector, and wherein a connecting portion between the first end and the second end of the actuator is pivotably connected to at least one of the first component or the second component, such that the actuator is capable of pivoting around the connecting portion by operating the button connector.

14. The trigger assembly according to claim 2, wherein the first component comprises a first helical portion, and the second component comprises a second helical portion, a helical end surface of the second helical portion being capable of mating with a helical end surface of the first helical portion, and wherein the first and second helical portions are configured to be movable to the preloaded position in the case where the second component rotates relative to the first component in the first direction along the mating first and second helical portions.

15. The trigger assembly according to claim 14, wherein at least one of the first helical portion or the second helical portion is configured such that the second helical portion is disengaged from the first helical portion in the case where the second component has been moved to the preloaded position.

16. The trigger assembly according to claim 15, wherein the actuator is configured to abut against the second helical portion to block the second component from leaving the preloaded position when the second helical portion is disengaging from the first helical portion.

17. The trigger assembly according to claim 14, wherein the helical end surface of the second helical portion is attached to the helical end surface of the first helical portion in the case where the second component has been moved to the triggered position.

18. The trigger assembly according to claim 14, wherein the first helical portion comprises two centrally symmetrical first helical portions, and the second helical portion comprises two centrally symmetrical second helical portions, and wherein the actuator comprises a first actuator and a second actuator arranged on two circumferential sides of at least one of the first component or the second component, and the first actuator and the second actuator are respectively configured to abut against a respective one of the two second helical portions.

19. An inhaler, comprising a trigger assembly configured to trigger the inhaler to spray atomized fluid, the trigger assembly comprising:
   a first component;
   a second component, wherein the first component and the second component are configured such that the second component is capable of moving away from the first component to a preloaded position in the case where the second component rotates relative to the first component in a first direction; and
   a backstop member, which is retractably arranged in the first component to block the rotation of the second component in a second direction opposite to the first direction in the case where the second component has been moved to the preloaded position,
   wherein the second component is capable of moving from the preloaded position towards the first component to a triggered position.

20. The inhaler according to claim 19, wherein the first component is constructed as an upper housing of the inhaler, the second component is constructed as a delivery tube socket of the inhaler, and wherein the delivery tube socket is configured to be rotatable with rotation of a lower housing of the inhaler.

* * * * *